(12) United States Patent
Minion

(10) Patent No.: US 10,335,296 B2
(45) Date of Patent: Jul. 2, 2019

(54) GRAFT WITHIN A GRAFT ENDOLUMINAL GRAFT

(75) Inventor: David J. Minion, Lexington, KY (US)

(73) Assignee: THE UNIVERSITY OF KENTUCKY RESEARCH FOUNDATION, Lexington, KY (US)

( * ) Notice: Subject to any disclaimer, the term of this patent is extended or adjusted under 35 U.S.C. 154(b) by 545 days.

(21) Appl. No.: 13/474,307

(22) Filed: May 17, 2012

(65) Prior Publication Data

US 2012/0296406 A1    Nov. 22, 2012

Related U.S. Application Data

(60) Provisional application No. 61/487,050, filed on May 17, 2011.

(51) Int. Cl.
| | |
|---|---|
| *A61F 2/852* | (2013.01) |
| *A61F 2/07* | (2013.01) |
| *A61F 2/95* | (2013.01) |
| *A61F 2/89* | (2013.01) |

(52) U.S. Cl.
CPC ............... *A61F 2/852* (2013.01); *A61F 2/07* (2013.01); *A61F 2/89* (2013.01); *A61F 2/95* (2013.01); *A61F 2002/9534* (2013.01)

(58) Field of Classification Search
CPC .............. A61F 2002/9534; A61F 2/852; A61F 2002/067; A61F 2002/828; A61F 2002/826; A61F 2002/30329; A61F 2250/0063; A61F 2250/006; A61F 2250/0065; A61F 2250/0039; A61F 2200/0075; A61F 2002/91591

USPC ................................................ 623/1.11–1.54
See application file for complete search history.

(56) References Cited

U.S. PATENT DOCUMENTS

| | | |
|---|---|---|
| 5,628,788 A | 5/1997 | Pinchuk |
| 6,030,415 A | 2/2000 | Chuter |
| 6,162,246 A | 12/2000 | Barone |
| 6,348,066 B1 | 2/2002 | Pinchuk et al. |
| 6,395,019 B2 | 5/2002 | Chobotov |
| 6,752,825 B2 | 6/2004 | Eskuri |
| 7,044,962 B2 | 5/2006 | Elliott |
| 7,122,052 B2 | 10/2006 | Greenhalgh |
| 7,297,156 B2 | 11/2007 | Nelson |

(Continued)

FOREIGN PATENT DOCUMENTS

EP    0646365 A1    4/1995

OTHER PUBLICATIONS http://dictionary.reference.com/browse/circumference.*

*Primary Examiner* — Diane D Yabut
*Assistant Examiner* — Socrates L Boutsikaris
(74) *Attorney, Agent, or Firm* — King & Schickli, PLLC

(57) ABSTRACT

A segmented endograft includes at least one positioning segment and at least one main body segment which are separately deployable. The at least one positioning segment and at least one main body segment may be connected one to another. For example, the at least one positioning segment and at least one main body segment may be connected along a portion of a circumference thereof, but unconnected along a remainder of the circumference thereof. The at least one positioning segment overlaps a portion of the at least one main body segment. Deployment systems may include the segmented endograft and the segmented endograft may be deployed according to various methods.

10 Claims, 4 Drawing Sheets

(56) References Cited

U.S. PATENT DOCUMENTS

| | | |
|---|---|---|
| 8,257,430 B2 * | 9/2012 | Mead .......................... 623/1.35 |
| 2001/0047198 A1 * | 11/2001 | Drasler .................... A61F 2/07 623/1.13 |
| 2002/0198587 A1 * | 12/2002 | Greenberg et al. .......... 623/1.13 |
| 2003/0149471 A1 | 8/2003 | Briana et al. |
| 2005/0113905 A1 * | 5/2005 | Greenberg ................ A61F 2/07 623/1.16 |
| 2006/0217796 A1 * | 9/2006 | DiMatteo .................. A61F 2/06 623/1.16 |
| 2010/0292775 A1 | 11/2010 | Kerr |

* cited by examiner

GRAFT WITHIN A GRAFT ENDOLUMINAL GRAFT

This application claims the benefit of priority in U.S. Provisional Patent Application Ser. No. 61/487,050, filed on May 17, 2011, the entirety of which is incorporated herein by reference.

TECHNICAL FIELD

The present disclosure relates generally to endoluminal grafts. More particularly, the disclosure relates to endoluminal grafts including at least one separately deployable portion facilitating remote positioning and repositioning of the device within the lumen of a blood vessel.

BACKGROUND OF THE INVENTION

It is known to provide endoluminal grafts or endografts for treating vascular lesions or pathologies such as aneurysms, stenosis, dissections, and others using minimally invasive surgical techniques. A conventional endograft is typically radially compressed or constrained, mounted on a deployment catheter, introduced into the vasculature, and advanced to its intended deployment site. Such conventional endografts, as is known in the art, typically include a metal lattice element (stent) which provides an expansile force and a fabric (graft) designed to contain pressurized bloodflow within its lumen, thereby excluding bloodflow from the site of the vascular pathology or lesion. As is known, the stent and graft portion of the endograft are typically attached one to the other or incorporated one with the other, leading to the common nomenclature "stent graft." Suitable materials for fabricating such endografts are well known in the art.

Typically, endografts are introduced into the vasculature from a location remote from the intended treatment zone, for example a femoral artery. The endograft must then be positioned and deployed so with the graft proximal and distal ends bracketing the vascular lesion, further whereby each graft end is positioned in a healthy portion of the blood vessel being treated, to provide an occlusive seal. This allows exclusion of the systemic blood pressure from the diseased blood vessel segment. Inaccurate placement of an endograft can result in ischemic complications from unintended coverage of branch vessels, or incomplete exclusion of the pathology being treated because of minimal apposition of the endograft and the vessel wall in the sealing zone. Further complicating the issue, the intervening healthy "landing zone" between the vascular pathology and potentially important branch blood vessels is often very short.

In cases such as minimal "landing zones" for proper placement of an endograft, the ability to re-position the device prior to final placement can improve accuracy and greatly improve the odds of safe and effective exclusion of the diseased vascular segments. However, during deployment, endografts are subjected to the displacement forces of the pressurized bloodflow in the vessel being treated, creating a "windsock" effect. Such displacement forces continue until the endograft is fully deployed or opened and blood flow is established through the endograft lumen. For conventional single piece endografts, however, at that point the endograft has been disconnected from the positioning device (such as a deployment catheter) and cannot be repositioned.

Strategies have been proposed for overcoming this problem. These include temporarily arresting bloodflow (for example by arresting the heart). However, this poses a significant patient risk. Another strategy considered is partially constraining the endograft longitudinally during deployment. However, a single piece endograft that is partially constrained longitudinally is still significantly detached from its deployment catheter, limiting the repositioning force that can be applied to the graft by manipulation of its deployment catheter at the remote introduction site.

There has accordingly been identified a need in the art for an endoluminal graft which, while effective for its intended purpose, provides additional advantages in allowing repositioning during placement in a diseased blood vessel, to ensure the best positioning of the device to isolate the vascular pathology being treated.

SUMMARY OF THE INVENTION

In accordance with the foregoing need identified in the art as described herein, an endoluminal graft or endograft is provided. The disclosed endograft includes at least one separately deployable portion for remote positioning and repositioning of the device within the lumen of a blood vessel. Advantageously, this feature facilitates the positioning, repositioning, and deployment of the device at a site of a lesion or pathology in a body lumen, for example vascular aneurysms, stenosis, dissections, and the like.

In one aspect, the disclosure relates to a segmented endograft including at least one positioning segment and at least one main body segment, each being separately deployable. The at least one positioning segment and the at least one main body segment are partially connected one to the other, typically along a portion of a circumference thereof, but are separate one from the other along a remainder of the circumference. An overlap is defined between adjoining portions of the at least one positioning segment and the at least one main body segment.

In the following description there are shown and described several different embodiments of this invention, simply by way of illustration of some of the modes best suited to carry out the invention. As it will be realized, the invention is capable of other different embodiments and its several details are capable of modification in various, obvious aspects all without departing from the invention. Accordingly, the drawings and descriptions will be regarded as illustrative in nature and not as restrictive.

BRIEF DESCRIPTION OF THE DRAWINGS

The accompanying drawings incorporated herein and forming a part of the specification, illustrate several aspects of the present invention and together with the description serve to explain certain principles of the invention. In the drawings.

Reference will now be made in detail to the present preferred embodiments of the invention, examples of which are illustrated in the accompanying drawings.

DETAILED DESCRIPTION OF THE INVENTION

In accordance with the foregoing need identified in the art as described herein, an endoluminal graft or endograft is provided. The disclosed endograft includes at least one separately deployable portion for remote positioning and repositioning of the device within the lumen of a blood vessel. Advantageously, this feature facilitates the positioning, repositioning, and deployment of the device at a site of a lesion or pathology in a body lumen, for example vascular aneurysms, stenosis, dissections, and the like.

Figure 1A:
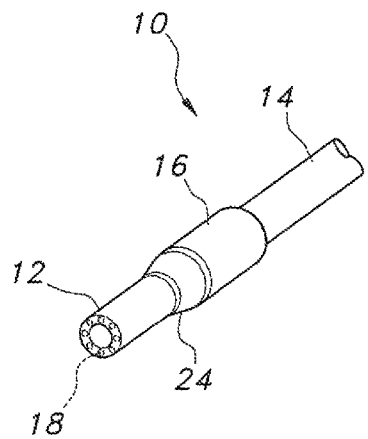
FIGS. 1a and 1b show a fully constrained segmented endograft according to the present disclosure in perspective and side cross-sectional view.
Figure 1B:
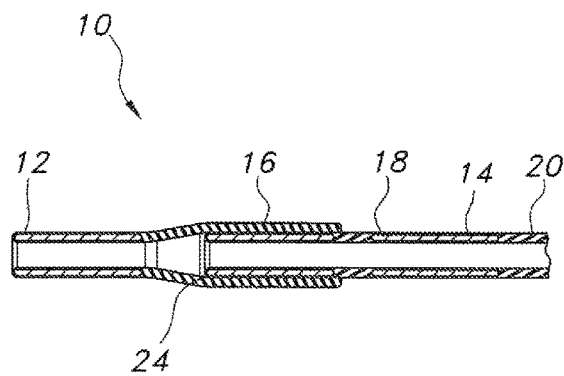

In one aspect, a segmented endograft 10 is provided. As shown in FIGS. 1a and 1b, the endograft 10 includes at least one positioning segment 12 and at least one main body 14, with positioning segment 12 defining an overlap 16 at adjoining portions of the two segments. The endograft 10 may be fabricated of overlapping or integrated stent materials 18 and graft materials 20 (see FIG. 1b), as is well known in the art, wherein the stent material 18 comprises a metal (or other suitable material) lattice structure which provides the expansile force when the endograft is deployed. In turn, the graft material 20 contains pressurized blood flow within a lumen 22 thereof, thereby isolating that blood flow from a diseased body lumen section.

In an embodiment (see especially FIG. 1b), positioning segment 12 and main body segment 14 may include integrated stent materials 18 and graft materials 20, but overlap 16 may be fabricated to include only graft materials 20. Any suitable material or combination of materials for use as stent and graft material, respectively, are contemplated. Lumen 22 also receives a deployment catheter (not shown) of known configuration for delivering the endograft 10 to a site of a body lumen lesion or pathology. In turn, as is also known in the art, the deployment catheter will likewise define a central lumen for receiving a guidewire of known design and material, for use in guiding the deployment catheter and associated endograft 10 to the site of the body lumen lesion or pathology. Of course, other methods of delivery of an endograft 10 are known, for example a dilation catheter (not shown) of known design.

Figure 2A:
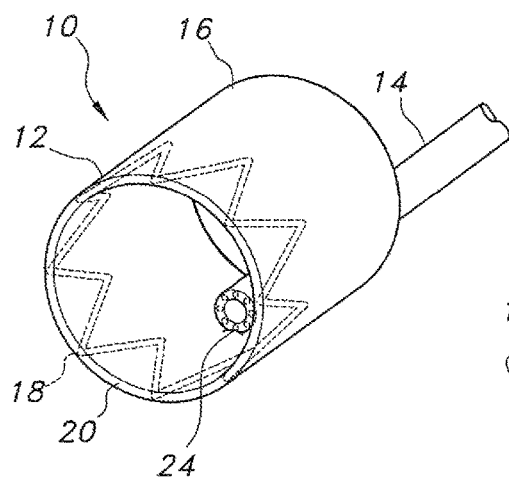
FIGS. 2a and 2b show the endograft of FIG. 1, with a positioning segment deployed, with FIG. 2a showing the deployed positioning segment in perspective view, and FIG. 2b showing the deployed positioning segment in a side cross-sectional view.
Figure 2B:
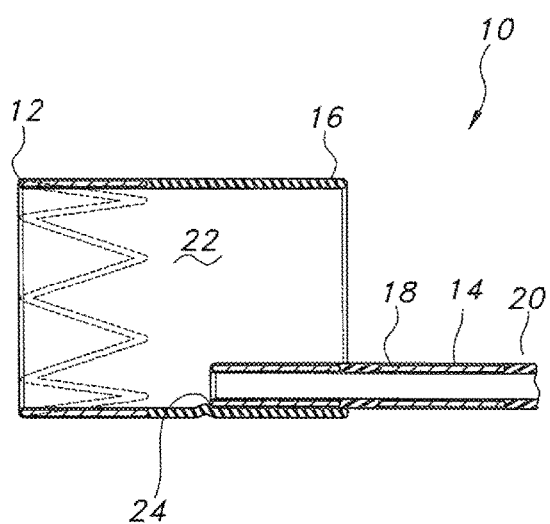

The positioning segment 12 and the main body segment 14 of the endograft 10 are partially connected at adjoining portions thereof, such as at attachment 24 (best seen in FIGS. 2 and 3). As best seen in FIGS. 2a and 2b, this may be accomplished by attaching a portion of an exterior circumference of a distal end of main body segment 14 to an interior lumen 22 of positioning segment 12. In that fashion, positioning segment 12 and main body segment 14 are connected one to the other along a portion of a circumference thereof, but remain unconnected along the remainder of their circumferences.

Figure 4A:
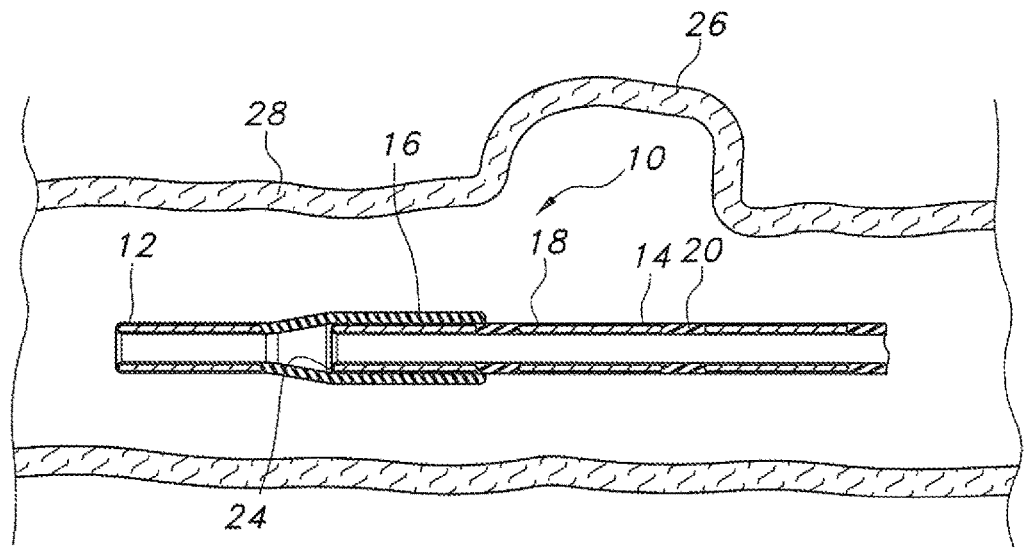
FIGS. 4a through 4c depict placement and deployment of the endograft of FIG. 1 to isolate a lesion such as a vascular aneurysm.
Figure 4B:
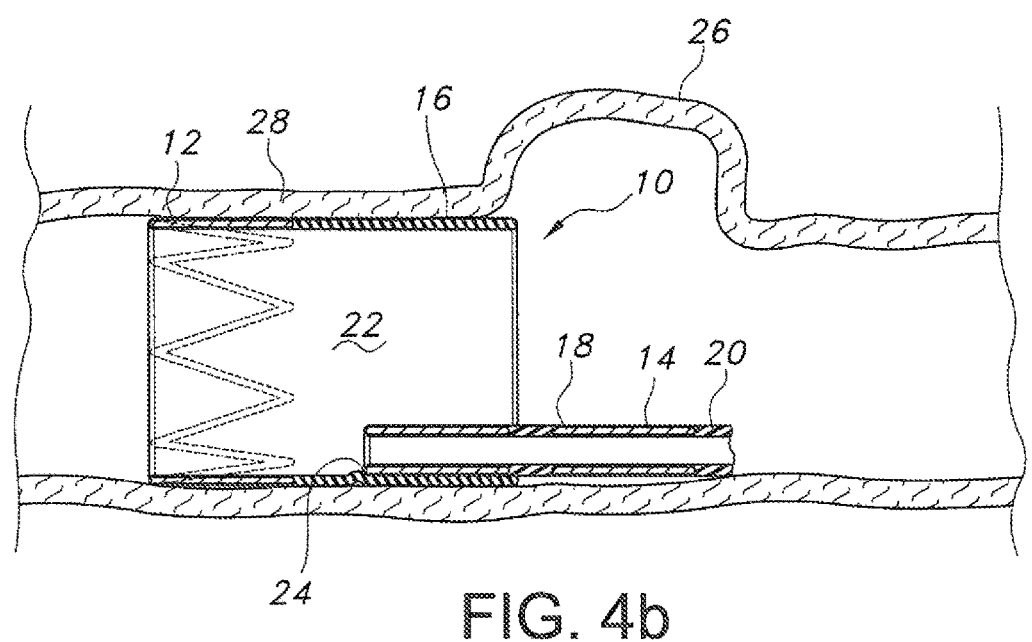
Figure 4C:
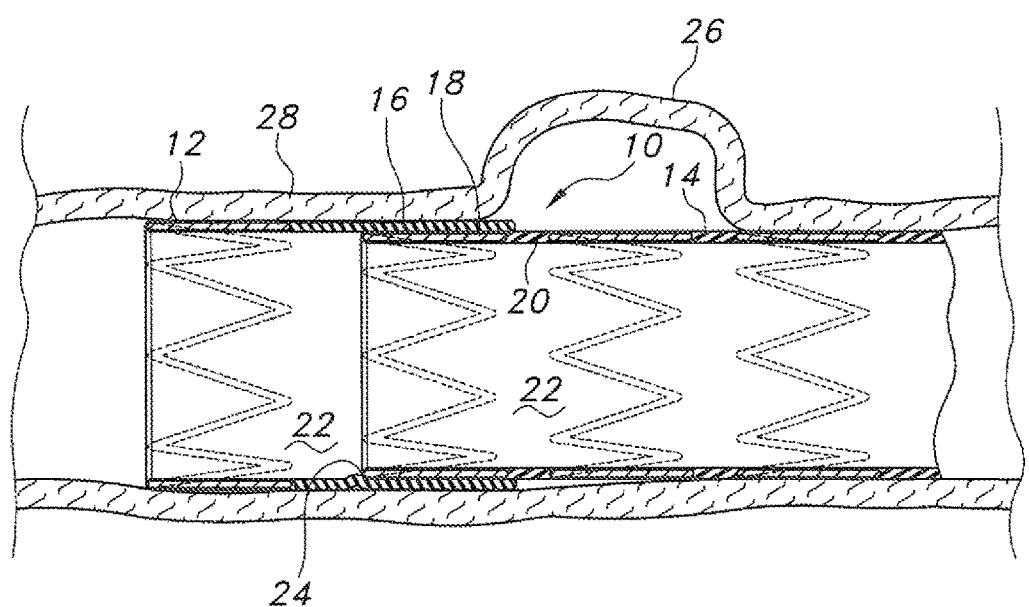

In use, the endograft 10 may be delivered to a site of a body lumen lesion or pathology (see FIGS. 4a-4c) by methods well known in the art. For example, the constrained endograft 10 may receive a deployment catheter or balloon dilation catheter in lumen 22 thereof. As discussed above, the deployment catheter or balloon dilation catheter will typically include a central lumen for receiving a guidewire therein. The guidewire may be introduced into the body from a remote site, for example a femoral artery, and advanced to the site of the lesion or pathology via one or more body lumens, for example via vasculature. Next, the assembled deployment catheter/endograft 10 may be advanced to the site of the lesion or pathology by sliding the assembly over the guidewire. Alternatively, the endograft 10 may be delivered and deployed by a balloon dilation catheter as is known in the art, Of course, it is contemplated to monitor each step of delivery and deployment, such as by known means including without limitation radiography, x-ray fluoroscopy, intravascular ultrasound, and the like, to confirm proper placement.

On reaching the site of a body lumen lesion or pathology such as an aneurysm 26 in a wall of a blood vessel 28 (see FIGS. 4a-4c), the endograft 10 is advanced until at least the positioning segment 12 is positioned distally to the lesion or pathology relative to the site at which the guidewire and deployment catheter were introduced. Then, the positioning segment 12 and overlap 16 are deployed (see FIGS. 2a, 2b, and 4b). Any suitable methods of deployment are contemplated to deploy/expand positioning segment 12. For example, use of one or more balloons of a balloon dilation catheter of known design is contemplated, and also use of self-expanding stent scaffold configurations (zig-zag stents, etc.) or shape memory alloys. Again, proper initial placement of the positioning segment 12 of endograft 10 may be monitored by any suitable means including visually, such as by radiography and the like.

The skilled artisan will appreciate that positioning segment 12, once deployed against the wall 28 of the body lumen, will assist in keeping the endograft 10 in place but since less surface area of the endograft 10 is in contact with an interior surface of the body lumen, will also facilitate any repositioning of the endograft 10 which may be required for optimal placement. In turn, the deployed positioning segment 12 also will allow blood flow through the lumen 22 thereof, thereby minimizing displacement of the device by pressurized blood flow and further facilitating repositioning of the endograft 10 as needed (with concurrent monitoring) to ensure optimal placement of the endograft 10 over the lesion or pathology. Because positioning segment 12 is connected to main body segment 14 via attachment 24, the two segments remain coupled allowing more efficient manipulation from the remote introduction site via the deployment catheter or dilation catheter, and also application of greater force in repositioning the device with less concomitant concern about damage to the body lumen interior such as would be expected from a fully deployed conventional endograft.

Further, the endograft 10 may be remotely positioned and repositioned as needed for optimal placement according to the positioning, size, etc. of the lesion or pathology, the proximity of the lesion or pathology to vascular branching, etc. using the deployment catheter or balloon dilation catheter, which remains encased in the constrained main body segment 14. In contrast, a conventional endograft, once deployed, can no longer be manipulated using an associated deployment catheter or the like, in that the lumen of the endograft is enlarged and no longer in contact with the catheter. As such, any manipulation of a conventional endograft for repositioning same can only be done by manipulating the endograft itself, which is inherently less efficient.

Figure 3A:
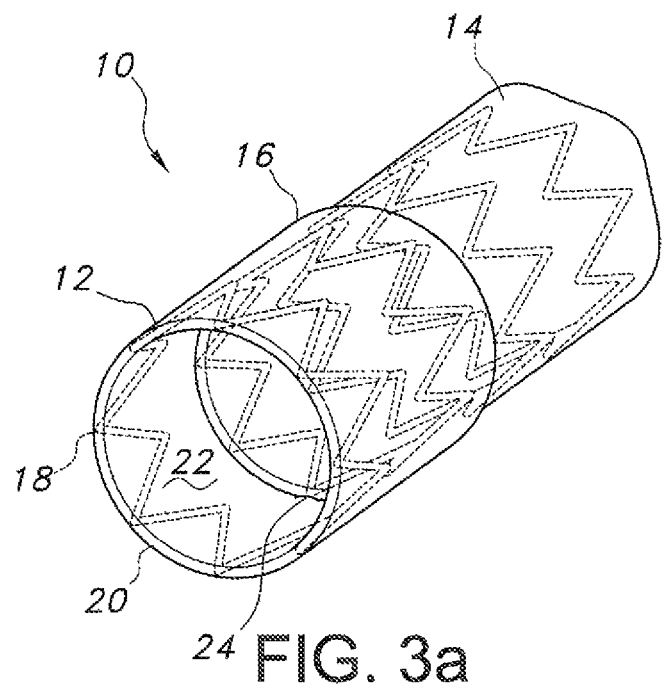
FIGS. 3a and 3b show the endograft of FIG. 1 fully deployed, with FIG. 3a showing a perspective view and FIG. 3b showing a side cross-sectional view.
Figure 3B:
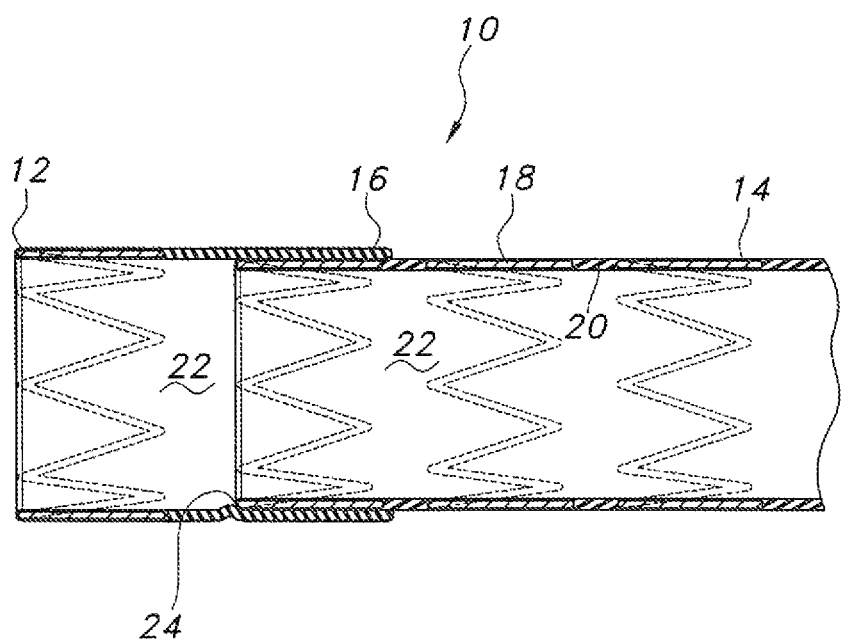

On verification of proper placement, main body 14 is deployed (see FIGS. 3a and 3b) by any suitable method as was described for positioning segment 12, i.e. balloons, self-expanding stent material, shape memory alloy stent material, etc. For example, the balloon used to deploy positioning segment 12 may be repositioned to deploy main body segment 14, or a second balloon may be used. As best shown in FIGS. 3a and 3b, on deployment an exterior surface of main body 14 contacts an interior surface of overlap 16, thereby forming a tight seal to prevent leakage of fluid passing through lumen 22. In turn, exterior surfaces of positioning segment 12, overlap 16, and main body 14 then contact interior surfaces of the wall 28 of the body lumen being repaired, enlarged, etc.

The deployed endograft 10 may optionally then be further enlarged, such as by a larger balloon, to provide additional contact with the body lumen wall 28 interior and to anchor proximal and distal ends of the endograft 10 above and below the body lumen lesion or pathology, in contact with healthy body lumen tissue, to provide the desired occlusive seal and to isolate the lesion or pathology from blood flow. Similar techniques may be employed as are known in the art when the desired effect is also to enlarge a body lumen such as that of a blood vessel, for example to relieve stenoses. Of course, other methods for anchoring the deployed endograft 10 to the wall 28 of the body lumen are known and contemplated for use herein, such as providing barbs (not shown) protruding from the stent material 18 which engage the wall 28.

It will be appreciated that the present endograft 10 provides significant advantages compared to conventional one-piece endoluminal grafts. The multi-segmented configuration, with separately deployable portions, facilitates remote positioning and repositioning of the device, ensuring the most accurate placement for isolation or exclusion of diseased body lumen tissue. Deployment of only a portion of the endograft 10 during such repositioning minimizes displacement of the device by pressurized bloodflow and also maintains physical coupling of the undeployed portion of the endograft to, e.g., a guidewire to allow manipulation of the endograft at areas of body lumen angulation. In turn, the need to resort to conventional strategies for eliminating or reducing displacement of the device by bloodflow during such repositioning, such as temporarily arresting blood flow, longitudinal constraint of the endograft during deployment, etc., is obviated.

The foregoing description of preferred embodiments has been presented for purposes of illustration and description. It is not intended to be exhaustive or limiting to the invention to the precise forms disclosed. Obvious modifications or variations are possible in light of the above teachings. For example, the depicted embodiments show a substantially tubular or cylindrical endograft 10, but it is also known in the art to provide such devices in a bifurcated or branched configuration, as a tapered structure, etc. in turn, additional deployable endograft 10 segments may be provided if necessary or desirable according to the size and positioning (relative to other body lumens) of the body lumen lesion or pathology.

The embodiments were chosen and described to provide the best illustration of the principles described herein and their practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

What is claimed is:

1. A segmented endograft, comprising:
   at least one positioning segment defined by a positioning segment wall and including a first cylindrical section; and
   at least one main body segment having a main body segment wall and including a second cylindrical section;
   wherein the first cylindrical section of the at least one positioning segment and the second cylindrical section of the at least one main body segment overlap one another along an entire length of both of the first cylindrical section and the second cylindrical section along a longitudinal axis of the segmented endograft and are fixedly attached to one another at only a portion of each of a circumference of the first cylindrical section and a circumference of the second cylindrical section, but are not attached to one another at a remainder of each of the circumference of the first cylindrical section and the circumference of the second cylindrical section;
   wherein the at least one positioning segment is independently deployable with respect to the at least one main body segment; and
   further wherein on deployment of both the at least one positioning segment and the at least one main body segment, the at least one positioning segment and the at least one main body segment define a fluid-impervious lumen passing through the at least one positioning segment and the at least one main body segment.

2. The segmented endograft of claim 1, wherein the at least one positioning segment and the at least one main body segment each comprise at least one stent material and at least one graft material, and the overlap comprises only at least one graft material.

3. The segmented endograft of claim 1, wherein the main body segment wall is disposed at least partially within the positioning segment wall.

4. The segmented endograft of claim 1, wherein on independent deployment of the at least one positioning segment, the at least one positioning segment and the at least one main body segment do not define the fluid-impervious lumen until independent deployment of the at least one main body segment.

5. An endograft delivery system, comprising:
   a segmented endograft comprising at least one positioning segment defined by a positioning segment wall, said positioning segment wall including a first cylindrical portion, and at least one main body segment defined by a main body segment wall, said main body segment wall including a second cylindrical portion;
   a deployment catheter configured to carry the endograft and to be endoluminally advanced through a body lumen from a remote introduction site to a site of a body lumen lesion or pathology; and
   a guidewire for guiding the deployment catheter;
   wherein the first cylindrical portion of the at least one positioning segment and the second cylindrical portion of the at least one main body segment overlap one another along an entire longitudinal length of each of the first and second cylindrical portions and are fixedly attached to one another at only a portion of the first cylindrical portion and the second cylindrical portion, but are not attached to one another at a remainder of each of the first cylindrical portion and the second cylindrical portion;
   wherein the at least one positioning segment is independently deployable with respect to the at least one main body segment; and
   further wherein only upon deployment of both the at least one positioning segment and the at least one main body segment, the at least one positioning segment and the at least one main body segment define a tight seal therebetween, and wherein upon deployment of only the at least one positioning segment and not the at least one main body segment, said tight seal is not present.

6. The endograft delivery system of claim 5, wherein the at least one positioning segment and the at least one main body segment each comprise at least one stent material and at least one graft material, and the overlap comprises only at least one graft material.

7. The endograft delivery system of claim 5, wherein the main body segment wall is disposed at least partially within the positioning segment wall.

8. A method for deploying a segmented endograft, comprising:
   providing a segmented endograft, the segmented endograft comprising:
      at least one positioning segment defined by a positioning segment wall and including a first cylindrical section; and
      at least one main body segment having a main body segment wall and including a second cylindrical section;
      wherein the first cylindrical section of the at least one positioning segment and the second cylindrical section of the at least one main body segment overlap one another along an entire length of both of the first cylindrical section and the second cylindrical section along a longitudinal axis of the segmented endograft and are fixedly attached to one another at only a portion of each of a circumference of the first cylindrical section and a circumference of the second cylindrical section, but are not attached to one another at a remainder of each of the circumference of the first cylindrical section and the circumference of the second cylindrical section;
      wherein the at least one positioning segment is independently deployable with respect to the at least one main body segment; and
      further wherein on deployment of both the at least one positioning segment and the at least one main body segment, the at least one positioning segment and the at least one main body segment define a fluid-impervious lumen passing through the at least one positioning segment and the at least one main body segment;
   delivering the segmented endograft in an undeployed state from a remote introduction site to a site of a body lumen lesion or pathology;
   deploying the at least one positioning segment of the segmented endograft independent of the at least one main body segment at a site distal to the body lumen lesion or pathology relative to the introduction site;
   repositioning the segmented endograft as needed whereby a distal and a proximal end of the segmented endograft contact healthy body lumen tissue above and below the body lumen lesion or pathology; and
   deploying the at least one main body segment of the segmented endograft whereby the at least one positioning segment and the at least one main body segment define the fluid-impervious lumen passing through the at least one positioning segment and the at least one main body segment, to provide an occlusive seal of the body lumen whereby the body lumen lesion or pathology is isolated from a flow of blood.

9. The method of claim 8, wherein the steps of delivering the segmented endograft to the site of the body lumen lesion or pathology, deploying the at least one positioning segment, and repositioning the segmented endograft are monitored visually to confirm a proper deployment of the segmented endograft.

10. The method of claim 9, wherein the at least one positioning segment and the at least one main body segment each comprise at least one stent material and at least one graft material, and the overlap comprises only at least one graft material.

* * * * *